United States Patent [19]
Ishida

[11] Patent Number: 5,054,469
[45] Date of Patent: Oct. 8, 1991

[54] APPARATUS FOR DESTROYING CALCULUSES

[75] Inventor: Akinori Ishida, Kawasaki, Japan

[73] Assignee: Kabushiki Kaisha Toshiba, Kawasaki, Japan

[21] Appl. No.: 327,821

[22] Filed: Mar. 23, 1989

[30] Foreign Application Priority Data

Mar. 31, 1988 [JP] Japan ................................. 63-76096

[51] Int. Cl.$^5$ .......................................... A61B 17/22
[52] U.S. Cl. .................................................. 128/24 EL
[58] Field of Search ................ 128/24 A, 328, 660.03, 128/24 EL; 606/127, 128

[56] References Cited

U.S. PATENT DOCUMENTS

| | | | |
|---|---|---|---|
| 3,735,755 | 5/1973 | Eggleton et al. | 128/24 A |
| 4,315,514 | 2/1982 | Drewes et al. | 128/24 A |
| 4,368,410 | 1/1983 | Hance et al. | 128/24 A |
| 4,620,546 | 11/1986 | Aida et al. | 128/24 A |
| 4,757,820 | 7/1988 | Itoh | 128/24 A |
| 4,763,652 | 8/1988 | Brisson et al. | 128/24 A |
| 4,803,995 | 2/1989 | Ishida et al. | 128/660.03 |

FOREIGN PATENT DOCUMENTS

| | | |
|---|---|---|
| 0081051 | 6/1983 | European Pat. Off. . |
| 0244730 | 11/1987 | European Pat. Off. . |
| 3621935 | 1/1988 | Fed. Rep. of Germany ...... 128/328 |

OTHER PUBLICATIONS

Millman, *Microelectronics*, 632-35 (1979).

*Primary Examiner*—William E. Kamm
*Assistant Examiner*—Scott R. Akers
*Attorney, Agent, or Firm*—Oblon, Spivak, McClelland, Maier & Neustadt

[57] ABSTRACT

A method and apparatus for destroying calculuses with a human body which detects an expiration end period of the human body by a detector. A pulse generator generates a first drive pulse to drive destroying energy radiation in synchronism with a start point of the detected expiration end period. Succeeding the first pulse, another pulse generator generates a train of pulses at a rate as set by a pulse rate setting circuit. By utilizing the pulse train, the energy is repeatedly radiated to the location of the calculus during the detected expiration end period.

8 Claims, 4 Drawing Sheets

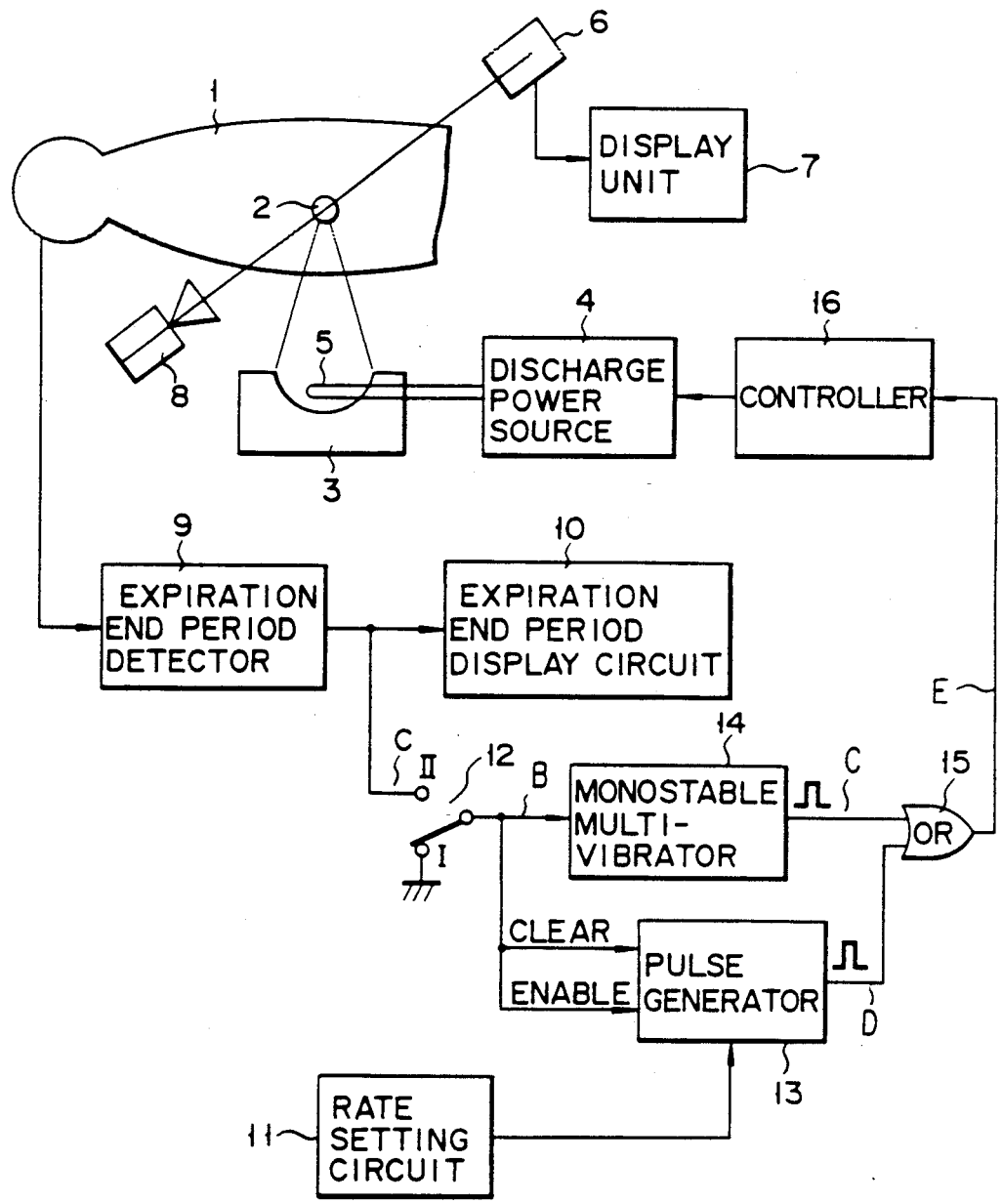
F I G. 1

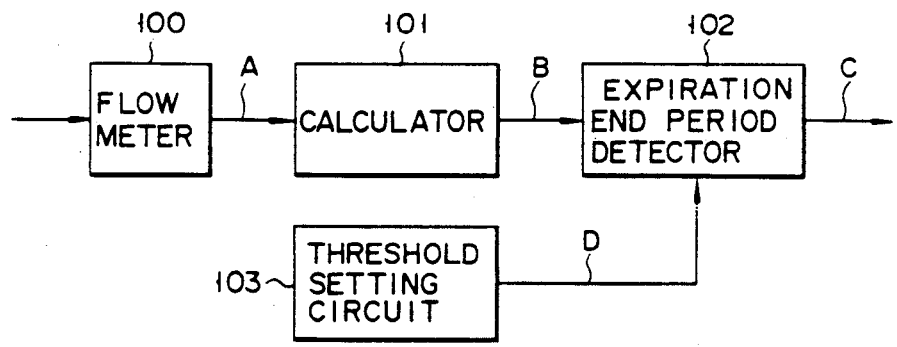
FIG. 2
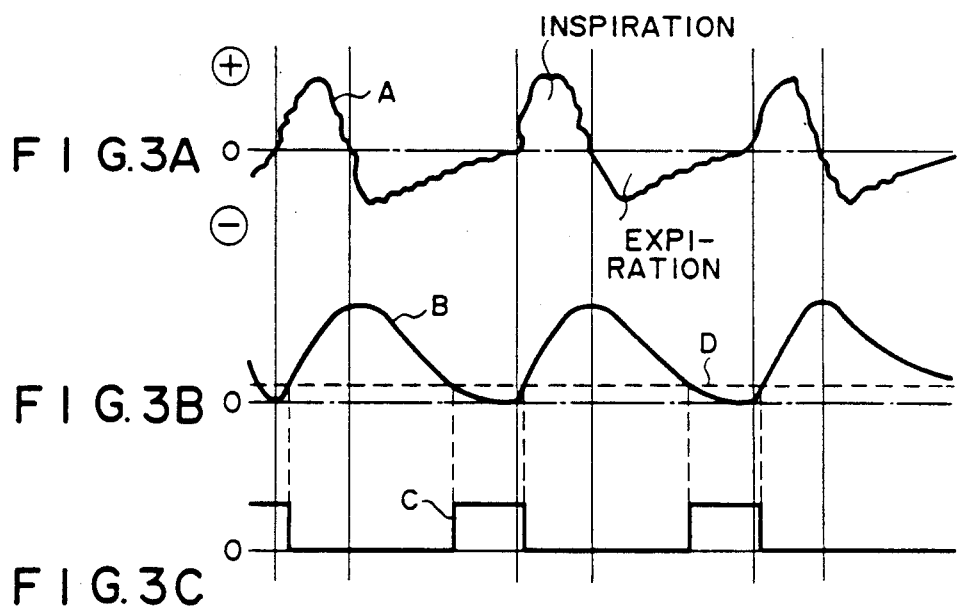
FIG. 3A
FIG. 3B
FIG. 3C

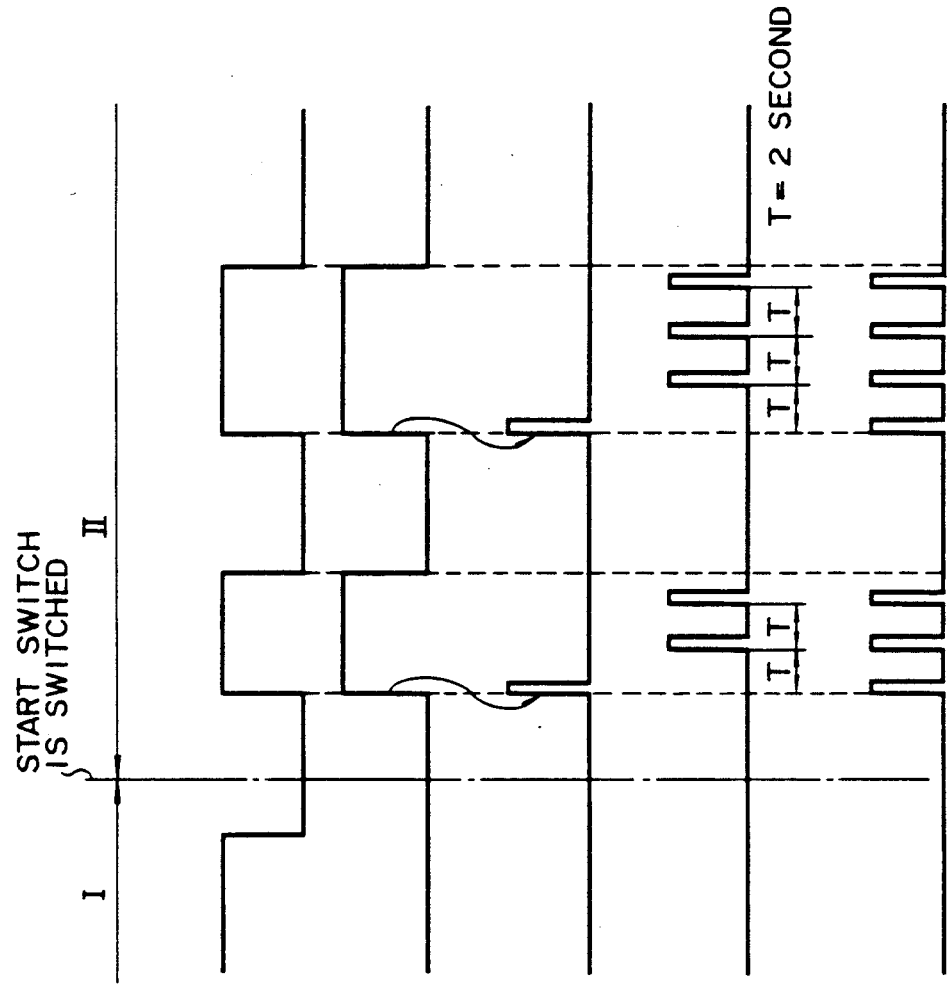

APPARATUS FOR DESTROYING CALCULUSES

BACKGROUND OF THE INVENTION

1. Field of the Invention

The present invention relates to an apparatus for destroying calculuses, of a type wherein a calculus present within a human body is disintegrated by externally applied energy.

A known apparatus for destroying calculuses comprises a generator for generating energy such as a focused shock wave or a focused ultrasonic wave, and an image processor for detecting the presence of a calculus existing within a human body and executing an appropriate processing for the purpose of breaking up the detected calculus. In operation, the apparatus searches for and detects a calculus within a human body, and upon detection of a calculus positions the focal point of destroying energy at the location of the detected calculus, and emits the destroying energy to disintegrate it. However, it is only a rare case that the calculus can be totally disintegrated by one application of the destroying energy. Normally the destroying energy is applied to the calculus repeatedly. However, during application of the energy, the human body respires, causing some body motion. Therefore, if the focal point of the radiated energy is set at where the calculus is first detected as being located, the calculus location, because progressing of the body motion, will become displaced from the focal point. Consequently, the radiation will then hit another part of the body, located off the affected part and possibly cause injury thereto.

A measure for overcoming the above problem is disclosed in Japanese Patent Disclosure No. 63-158049. In the technique disclosed, a period of an end portion in an expiration duration is detected since during this period, the affected part is only slightly displaced from the radiation focal point set. Thus, the expiration end period is used for the positioning of the focus of the radiation at the affected part, and for the generation of drive pulses for radiating the destroying energy, these pulses being generated repetitively at a preset rate (repetitive frequency). In other words, the calculus is disintegrated only during the expiration end period. When the drive pulse rate is, for example, 2 Hz, viz., the destroying energy is radiated every 0.5 sec., and the number of drive pulses that is required to disintegrate the calculus can be generated during the expiration end period. If the rate is lower than 2 Hz, for example, 0.5 Hz, that is, if the pulse is generated every 2 sec., the number of drive pulses generated during the expiration end period will be insufficient to produce enough radiated energy to disintegrate the calculus. It is assumed that the number of breathings is 12 per minute, a time of one breathing cycle is 5 sec., an expiration duration is 3 sec., and the expiration end period is 2 sec. In this instance, if the drive pulse rate is 0.5 Hz, this may give rise to an extreme case in which all the pulses required for disintegrating the calculus can not be generated during the expiration end period of 2 sec.

In particular, when the starting time point of the expiration end period is not coincident with the time point of generation of the first drive pulse, the number of pulses generated during the end period will be reduced.

Another example of prior art is found in the catalog of an extracorpreal urinary-passage stone lithotripsy device named "LITHOSTAR" manufactured by SIEMENS of West Germany. The catalogue describes a technique wherein shock waves are generated during a breathing gate in synchronism with the ECG in an electrocardiogram. However, it is not set forth in the catalog that the shock wave is generated in synchronism with a start point of the breathing gate. Therefore, there is the possibility that the calculus will move, due to body motion caused by breathing, from the focal point of the radiated breaking energy, and hence the energy will be applied to and adversely affects tissue near the calculus.

2. Summary of the Invention

Accordingly, an object of the present invention is to provide an apparatus for destroying calculuses and which is capable of generating drive pulses of a destroying energy within a predetermined period regardless of the preset rate for generating the drive pulses, and hence is free from the problem of injury possibly being caused to an unaffected part of the body by the mishitting of the destroying energy.

To achieve the above object, there is provided an apparatus for destroying calculuses comprising means for generating focused destroying energy, means for positioning a focus of the destroying energy at the position at which a calculus is located within the human body, means for detecting a radiation period of the destroying energy, means for generating a first drive pulse to drive the destroying energy radiation at a time point coincident with a start point of the radiation period, the first drive pulse generating means being coupled with the radiation period detecting means; and means for generating, during the radiation period, a train of drive pulses to repeatedly generate destroying energy at a predetermined rate, in succession to generation of the first drive pulses.

With such an arrangement, a first drive pulse is generated at a start point of a predetermined period, and a train of pulses is generated in succession within the same period. Thus, generation of the required number of drive pulses during the predetermined period is assured regardless of the pulse rate. Therefore, the problem inherent in the prior art, i.e. that the destroying energy hits another unaffected part of the body located near the affected part, with possibly adverse affects, is successfully overcome. Additionally, the present invention allows a speedy treatment to be realized.

BRIEF DESCRIPTION OF THE DRAWINGS

FIG. 1 is a block diagram showing an apparatus for destroying calculuses according to an embodiment of the present invention;

FIG. 2 is a block diagram of a detector for detecting an expiration end period, which is used in the apparatus of FIG. 1;

FIGS. 3A through 3C are waveforms of signals at output portions of respective units in the detector of FIG. 2;

FIGS. 4A through 4E are timing charts useful in explaining the operation of the detector of FIG. 2;

DETAILED DESCRIPTION OF THE PREFERRED EMBODIMENTS

Figure 5:
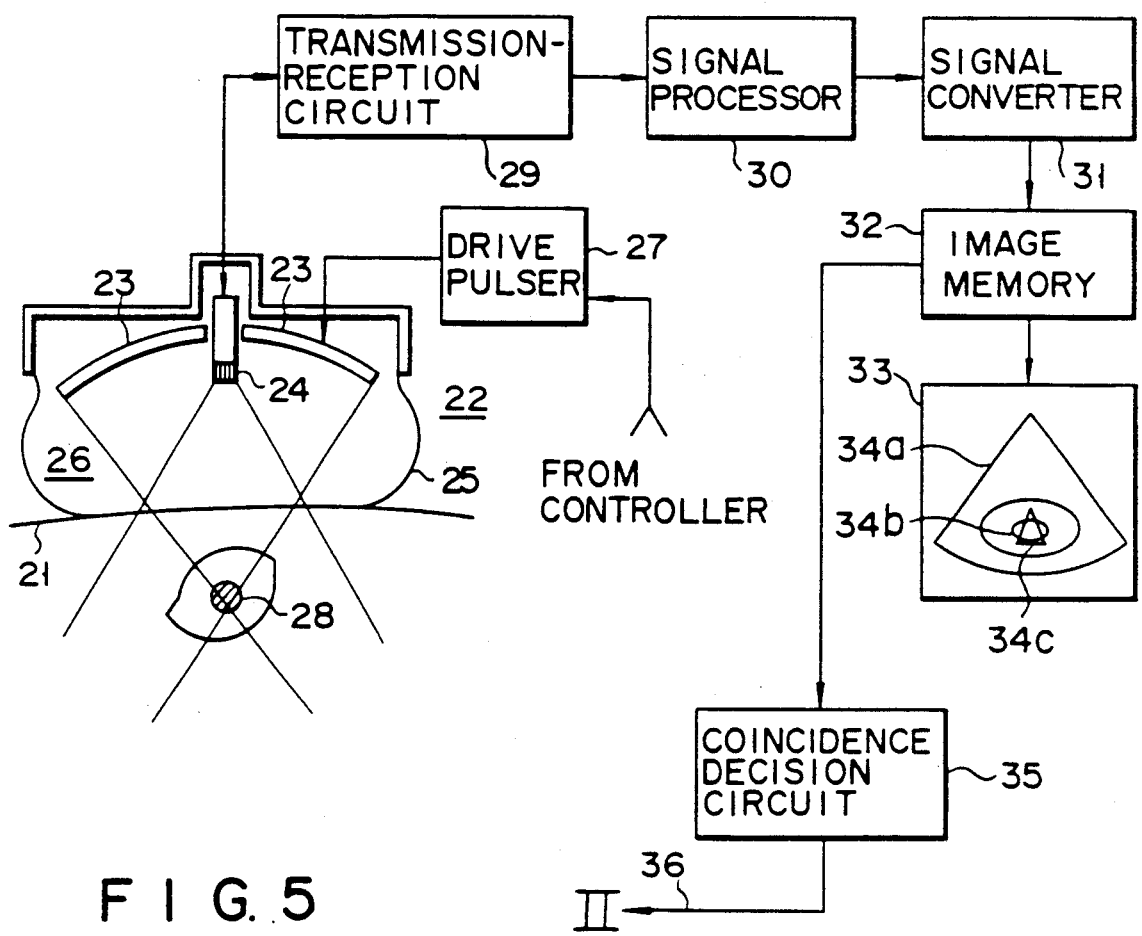
FIG. 5 is a block diagram showing an apparatus for destroying calculuses according to another embodiment of the present invention.

An apparatus according to the present invention for destroying calculuses within a human body by disintegration, using a shock wave energy as a destroying energy according to the present invention, will now be described with reference to the accompanying drawings.

FIG. 1 shows an arrangement of an apparatus for destroying calculuses according to an embodiment of the present invention. As shown, an ellipsoidal reflector 3 is arranged so that its focus is positioned on the location of a calculus 2 within a human body 1. In performing treatment, charges stored in a discharge power source 4 are discharged through a spark gap 5 located at a first focus point of the ellipsoidal reflector 3. The shock wave energy generated there is reflected by the ellipsoidal reflector 3 and is projected to the calculus 2 as a second focus of the ellipsoidal reflector. With the focus of the ellipsoidal reflector 3 positioned on the location of the calculus 2 within the human body 1, a display screen of a display unit 7 presents the information of the internal organs of the human body, as detected by an X-ray detector 6. An X-ray tube 8 and the detector 6 are disposed opposing each other with the human body 1 positioned therebetween. An operator moves the human body 1 while simultaneously viewing the display, and when the calculus 2 is positioned at the center of the display, the position of the human body 1 is fixed. The display unit 7 is arranged so that the center of the display screen indicates the second focus of the ellipsoidal reflector 3. Accordingly, when the center of the display coincides with the calculus displayed, the destroying energy is radiated toward the calculus, to thereby destroy the calculus.

An expiration end period detector 9 detects the expiration end period of a breathing period of the human body 1. A motion of the human body due to his breathing and, by extension a movement of the calculus, is relatively small during the expiration end period. During this period, therefore, the positioning of the focus relative to the calculus is performed and, as already stated, the timing of generation of the shock wave energy is decided.

A detailed arrangement of the expiration end period detector 9 will be described with reference to FIGS. 2 and 3. In FIG. 2, a flow meter 100 measures a respiratory flow caused by breathing, through a transducer (not shown) attached to a patient. A waveform of respiratory flow as denoted as A is illustrated in FIG. 3A. In this figure, (+) indicates a variation in the inspiratory flow and (−) indicates a variation in the expiratory flow. The result of respiratory flow measurement is supplied to a respiratory volumen calculator 101 which integrates the waveform A to obtain a waveform B, representing the respiratory volume shown in FIG. 3B. An expiration end period detector 102 compares the signal of the waveform B with a signal representative of a threshold value D (FIG. 3B), which is set by a threshold value setting circuit 103. A period that the waveform B is smaller than the threshold value D is produced in terms of an expiration period end signal C.

The operation of the apparatus for destroying calculuses thus arranged will now be described in connection with the operation of the apparatus. An expiration end period of a breathing period of a patient is detected by the expiration end period detector 9. Receiving the detect result, the display unit 10 presents the expiration end period in the form of a periodic tone or a light indicator to an operator. The operator then positions the location of the calculus detected within the patient at the second focus of the ellipsoidal reflector 3, viz. in the center of the display screen of the display unit 7. This operation is done while the operator sees the X-ray image on the display, and hears the periodic tone or sees the light indicator representing detection of the expiration end period. As a result, correct positioning of the calculus position is achieved during the expiration end period even though the calculus location may shift due to breathing by the patient. The next operation will then disintegrate the calculus. To this end, a rate setting circuit 11 is first operated to set the drive pulse rate at 0.5 Hz, for example. This figure indicates a low drive pulse rate, and that shock wave energy is radiated every 2 sec. Then, a start switch 12 is switched over from position I to position II. Reference is now made to FIGS. 4A to 4E. At the position I, the enable terminal and the clear terminal of a pulse generator 13, and the input terminal of a monostable multivibrator 14 are coupled with ground. In this state, the pulse generator 13 is not in the calculus disintegrating mode. When the switch 12 is turned to the position II manually or automatically, all the above terminals are connected to the expiration end period detector 9. When the expiration end period (the positive portion of the waveform C in FIG. 3C) is detected, the multivibrator 14 generates a first pulse (C) as shown in FIG. 4C. This pulse (C) is applied as a first pulse of pulses (E) (FIG. 4E) to a controller 16, by way of an OR gate 15. Then, the pulse generator 13 is enabled, to generate pulses (D) (FIG. 4D) recurring at the rate (as above, 0.5 Hz, appearing every 2 sec.) as already set by the rate setting circuit 11. The pulses (D) also pass through the OR gate 15 and, in succession to the pulse (C), go in the form of the pulses (E) to the controller 16. The above operation is performed during the expiration end period. When this period terminates, the pulse generator 13 is disabled, and a pulse outputting counter is also cleared, to be ready for the next expiration end period. Thus, during the expiration end period, the longest possible train of pulses (E) is applied at the set rate to the controller 16, which in turn, causes the discharge power source 4 to discharge the stored charges through the spark gap 5. The resultant shock wave energy is applied to the affected part, i.e. the calculus, and disintegrates it. Then, the operator confirms, by using the display unit 7, that the calculus has been disintegrated, and upon confirmation returns the switch 12 to the position I. At this point, the treatment operation performed by the apparatus for destroying calculuses according to this invention is completed.

In the above embodiment, a combination of the monostable multivibrator 14, pulse generator 13, and OR gate 15 is used for forming the pulse train of the set rate. If required, a train of pulses appearing at the start point of the expiration end period may be formed by use of a combination of a microcomputer and a timer.

Additionally, it should be evident that in the present invention focused ultrasonic energy may be used in place of shock wave energy.

A second embodiment of an apparatus for destroying calculuses according to the present invention, which uses focused ultrasonic energy as the destroying energy, will now be described with reference to FIGS. 5 and 6.

Figure 6:
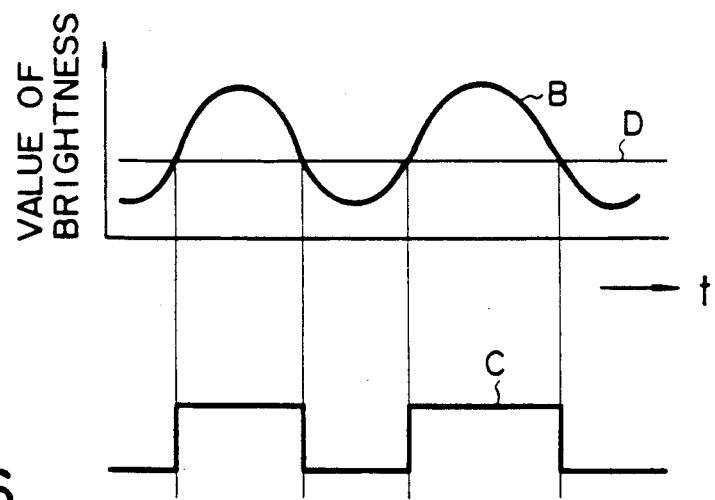
FIG. 6 shows waveforms for explaining the operation of a coincidence detect circuit for detecting a coincidence between the location of a calculus and the focus of ultrasonic wave energy.

As shown in FIG. 5, an applicator 22 is placed in contact with the surface of a human body 21. Within the applicator 22 are a disintegrating transducer 23 for breaking a calculus and an imaging ultrasonic probe 24 for imaging the calculus, as shown in FIG. 5. The imaging ultrasonic probe 24 is located at the center of the disintegrating transducer 23. The applicator 22 is hermetically sealed by a membrane 25. The applicator 22 thus formed is filled with a liquid of an appropriate acoustic impedance, for example, water 26. When the applicator 22 is placed in close contact with the surface of the human body 21, the focused ultrasonic energy radiates toward the inner organs of the human body 21. The disintegrating transducer 23 is coupled with a drive pulser 27 by way of a cable. The drive pulser 27 is driven with a control signal derived from a controller (not shown), to radiate focused ultrasonic energy into the human body 21.

The imaging ultrasonic probe 24 is excited so as to make a sector scan, for example. An echo signal resulting from the sector scan is then applied to a transmission/reception circuit 29. The output signal from the circuit 29 is applied to a signal processor 30, where it is amplitude detected, and the detected signal is applied in the form of a digital video signal to a converting system 31. The converting system 31, made up of a frame memory, line memory, etc., applies an appropriate signal processing to the digital video signal. The output signal from the converting system 31 is temporarily stored in an image memory 32, and is then applied to a TV monitor 33. Upon receiving the signal, the image memory 32 displays an acoustic domain image 34a in a sector fashion, an image 34b including a kidney, calculus, etc., and a focal marker 34c representing a focus of the ultrasonic energy transmitted from the disintegrating transducer 23.

The sector image (B-mode image) 34a on the TV monitor represents a calculus within a human body. The calculus image has a high acoustic impedance, and it therefore reflects the applied ultrasonic wave at a high intensity. The result is that the image 34b is brighter than the surrounding organic image The focal marker 34c is fixed on the monitor screen. The reason for this is that the disintegrating transducer 23 and imaging ultrasonic probe 24 are fixedly disposed as shown. Therefore, to position the calculus image 34b at the focal marker 34, all the operator has to do is to move the applicator 22 until it coincides with image 34b in position. To determine whether focal marker 34c does coincide with the calculus image 34b, a coincidence decision circuit 35 is provided. The decision circuit 35 works out the brightness value of the acoustic domain image (B-mode image) contained in the focal marker 34c region, which is then stored in the image memory 32, and outputs a coincidence-degree signal 36 every 5 sec., for example. More exactly, the coincident decision circuit 35 looks for a brightness value B in excess of a predetermined value of brightness D and produces the values B in the form of a degree-of-coincidence degree signal C. The duration of the signal C is used to represent the expiration end period. It is during this period that the disintegrating transducer is allowed to radiate the ultrasonic wave toward the calculus and the ultrasonic wave radiated, therefore, exactly hits the affected part, thereby eliminating the risk of injury to tissue near the calculus within the human body.

What is claimed is:

1. An apparatus for destroying calculuses comprising:
   means for generating focused destroying energy;
   means for positioning a focus of the destroying energy at a location of a calculus in a human body;
   means for detecting a period during which the location of the calculus coincides with the focus of the destroying energy;
   means for generating a first control pulse to control generation of the destroying energy at a time point coincident with a start point of said period, said first control pulse generating means being coupled with said period detecting means; and
   means coupled to said focused destroying energy generating means, for generating during said period of train of control pulses to repeatedly generate destroying energy at a predetermined rate, succeeding to the generation of said first control pulse.

2. An apparatus for destroying calculuses according to claim 1, wherein said period detecting means comprises means for detecting an expiration end period of a breathing pattern of said human body.

3. An apparatus for destroying calculuses according to claim 1, wherein said period detecting means comprises means for detecting the duration that a value of brightness of an image of said calculus exceeds a predetermined value of brightness.

4. An apparatus for destroying calculuses according to claim 1, wherein said means for generating a first pulse to control said destroying energy is a monostable multivibrator.

5. A method of lithotripsy for destroying calculuses in a human body by generating focused destroying energy comprising the steps of;
   positioning a focus of the focused destroying energy at a location of a calculus in said human body;
   detecting a period during which the location of the calculus coincides with the focus of the focused destroying energy;
   generating a first control pulse to control the generation of destroying energy at a time point coincident with a start point of said period; and
   generating during said period a train of control pulses to repeatedly generate destroying energy at a predetermined rate, succeeding to the generation of said first pulse.

6. A method according to claim 5, wherein said period detecting step comprises detecting an expiration end period of a breathing pattern of said human body.

7. A method according to claim 5, wherein said period detecting step comprises detecting the duration that the value of brightness of an image of said calculus exceeds a predetermined value of brightness.

8. A method according to claim 5, wherein said control pulse generating step is performed by a monostable multivibrator.

* * * * *